Nov. 24, 1970 J. A. FRITZ Plant Pat. 3,005
ALMOND TREE
Filed Feb. 19, 1969
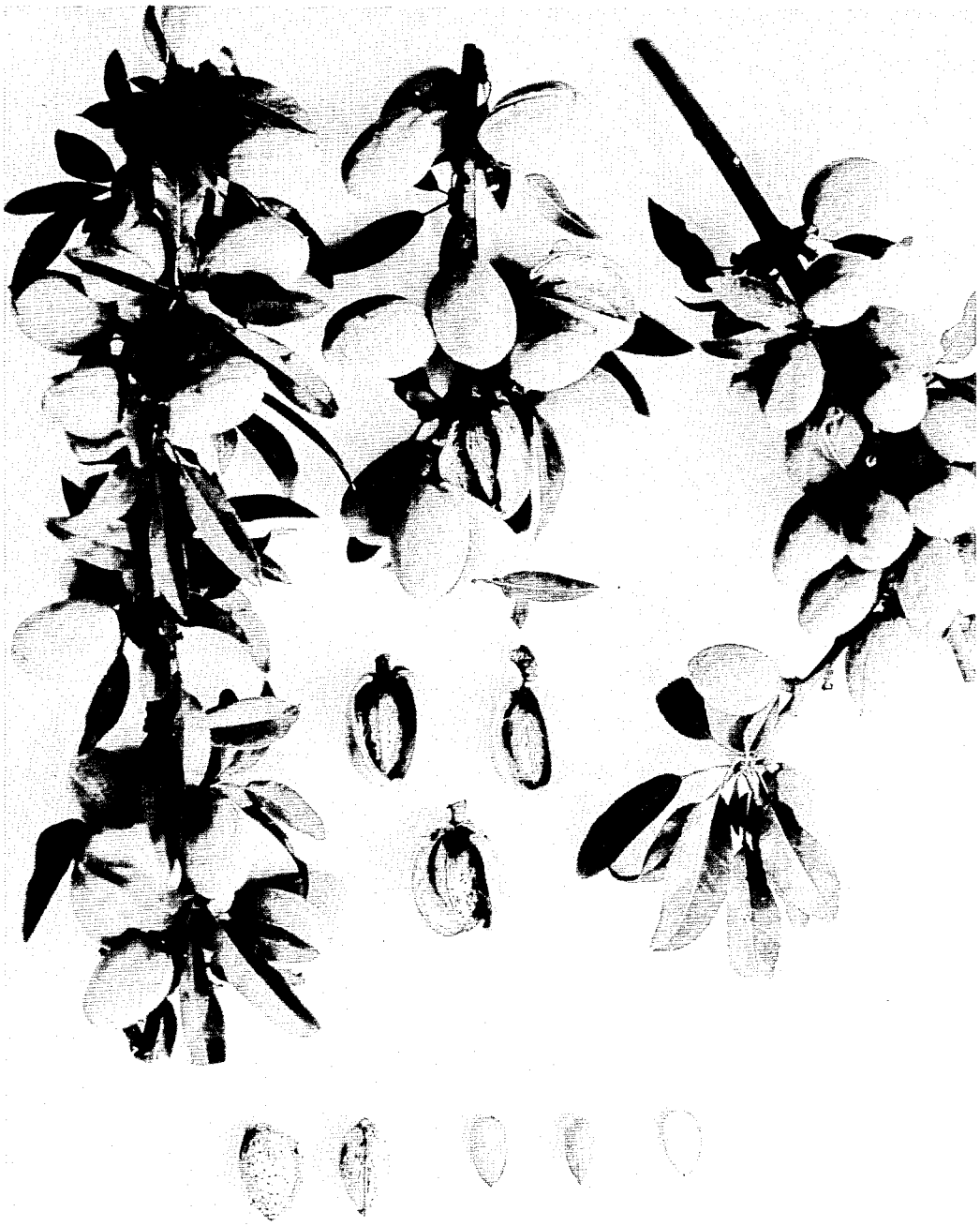
INVENTOR
John A. Fritz
BY
Webster & Webster
ATTORNEYS

United States Patent Office

Plant Pat. 3,005
Patented Nov. 24, 1970

3,005
ALMOND TREE

John A. Fritz, J 11691 E. Graves Road,
Manteca, Calif. 95336

Filed Feb. 19, 1969, Ser. No. 800,781
Int. Cl. A01h *5/03*
U.S. Cl. Plt.—30 1 Claim

ABSTRACT OF THE DISCLOSURE

A variety of almond tree of medium size and vigor, medium to upright growth, open with respect to density, and a regular and very heavy producer of small nuts well distributed on the tree; the nuts being easy to harvest and hull, and having a quite substantial percentage of kernel to shell.

ORIGIN OF THE VARIETY

The herein claimed variety of almond tree was discovered by me growing as a chance seedling on my ranch located near Manteca, County of San Joaquin, State of California. Subsequent to my discovery of such chance seedling, I maintained it under continuing observation, and which resulted in recognition by me of its novel and distinct characteristics.

ASEXUAL REPRODUCTION OF THE VARIETY

Upon recognizing said chance seedling as a new and distinct variety of almond tree, I asexually reproduced it by grafting onto a mature Ne Plus Ultra tree also growing on my ranch located as aforesaid; such asexual reproductions, when compared to the original tree, having run true to the same in all respects.

SUMMARY OF THE VARIETY

The present variety of almond tree is of medium size and vigor, medium to upright in growth, open with respect to density, and a regular and very heavy producer of small nuts which are easy to harvest and hull; the blooming period being approximately with the Nonpareil and the harvest approximately with the Mission.

The present variety of almond tree is additionally characterized by high production of small nuts having a relatively high—and hence commercially desirable—percentage of kernel to shell; the kernels likewise being quite small and thus well suited for use in the confection trade for inclusion in candy and the like.

The present variety of almond tree is also characterized by small nuts having an extremely low percentage of doubles.

The present variety of almond tree is further characterized by its ability to serve as an effective pollenizer for other varieties of almonds.

BRIEF DESCRIPTION OF THE DRAWING

The drawing is a photographic reproduction in color illustrating twigs with clusters of nuts remaining attached; detached nuts both in and out of hull; and kernels out of shell, with one kernel cut to expose the meat.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Open.
- *Size.*—Medium.
- *Vigor.*—Medium.

Trunk:
- *Form.*—Stocky.
- *Texture.*—Medium.

Branches:
- *Form.*—Medium.
- *Texture.*—Smooth.
- *Lenticels.*—Number: Medium. Size: Medium.
- *Branching habit.*—Medium to upright. Less upright than Mission (Texas).

Foliage:
- *Quantity.*—Medium.

Leaves:
- *Size.*—Medium. Average length (vigorous shoots): 88.4 mm. Average length (spurs): 66.0 mm. Average width (vigorous shoots): 26.7 mm. Average width (spurs): 17.0 mm.
- *Form.*—Lanceolate. Acutely pointed.
- *Thickness.*—Medium.
- *Texture.*—Smooth.
- *Margin.*—Crenate.
- *Petiole.*—Medium length. Medium thickness.
- *Rib.*—Pronounced.
- *Glands.*—Number: 3 to 6, average 4. Alternate. Positioned mainly on petiole, sometimes on base of blade.
- *Color.*—Top side: Medium green (22–K–7). Under side: Medium green (22–I–7).

Bloom:
- *Amount of bloom.*—Heavy.
- *Color.*—White.
- *Blooming period.*—Approximately with Nonpareil.

Crop:
- *Bearing.*—Regular bearer.
- *Productivity.*—Very heavy.
- *Distribution of nuts on tree.*—Well distributed.
- *Harvest period.*—October 1–15 in normal year. Approximately with Mission.
- *Tenacity.*—Easy to harvest. Easy to hull.

Hull:
- *Outer surface.*—Relatively smooth.
- *Pits.*—None.
- *Form.*—Regular.
- *Thickness.*—Thin, relatively thinner than Ne Plus Ultra.
- *Flesh.*—Tough.
- *Suture.*—Slightly ridged—more so than Nonpareil, less than Mission.
- *Dehiscence.*—Opens freely.
- *Splitting.*—Along suture.
- *Color.*—Light green (21–I–5), with a silvery sheen.

Nut:
- *Size.*—Small. Average length: 29.5 mm. Average width: 18.6 mm. Average thickness: 14.3 mm.
- *Form.*—Length/width: Ovate. Width/thickness: Plump, less than Mission, more than Nonpareil.
- *Shell.*—Soft. Medium thin. Smooth. Outer shell: Crumbling. Inner shell: Brittle, firm, well sealed.
- *Color.*—Straw (11–J–5).
- *Pits.*—Small. Few. Medium shallow. Round.
- *Base.*—Slightly ventrally oblique.
- *Stem.*—Small. Moderately acute.
- *Apex.*—Acute. Acuminate. Blunt. Slightly prolonged at tip.
- *Wing.*—Medium breadth. Medium thickness. Tapered toward base.
- *Inner surface.*—Medium colored.
- *Ventral streak.*—Medium dark. Broad. Medium length. Point: Obtuse.
- *Percentage of kernel to nut.*—49.9%.

Kernel:
- *Size.*—Small. Average length: 22.1 mm. Average width: 12.0 mm. Average thickness: .84 mm.

*Form.*—Length-width: Ovate. Width/thickness: Medium.
*Base.*—Moderately ventrally oblique.
*Stem scar.*—Small. Obtuse.
*Apex.*—Obtuse. Acuminate. Blunt. Slightly prolonged at tip.
*Plumpness.*—Medium smooth.
*Pellicle.*—Medium thickness.
*Pubescence.*—Very slight. Slightly veined.
*Color.*—Medium brown (14–L–10).
*Number of doubles.*—Few.
*Defective kernels.*—Very few.
*Flavor.*—Very, very slightly bitter.
*Quality.*—Good.

All prior varieties of almond trees named herein are unpatented.

The almond tree and its nuts herein described may vary in slight detail due to climatic and soil conditions under which the variety may be grown; the present description being of the variety as grown in the Central Valley of California.

What is claimed is:

1. A new and distinct variety of almond tree, substantially as illustrated and described, which is of medium size and vigor, medium to upright in growth, open with respect to density, in bloom approximately with the Nonpareil and a good pollenizer, in harvest approximately with the Mission, and a regular and very heavy producer of small nuts which are easy to harvest and hull, and which nuts have small kernels, a relatively high percentage of kernel to shell, and a low percentage of doubles.

No references cited.

ROBERT E. BAGWILL, Primary Examiner